US009089362B2

(12) United States Patent
Shturman (10) Patent No.: US 9,089,362 B2
(45) Date of Patent: Jul. 28, 2015

(54) ROTATIONAL ATHERECTOMY DEVICE WITH ECCENTRIC ABRASIVE ELEMENT AND METHOD OF USE

(71) Applicants: Cardio Flow Inc., Long Lake, MN (US); Lela Nadirashvili, Nyon (CH)

(72) Inventor: Leonid Shturman, Nyon (CH)

(73) Assignee: Cardio Flow, Inc., Long Lake, MN (US)

( * ) Notice: Subject to any disclaimer, the term of this patent is extended or adjusted under 35 U.S.C. 154(b) by 0 days.

(21) Appl. No.: 14/170,923

(22) Filed: Feb. 3, 2014

(65) Prior Publication Data

US 2014/0180317 A1    Jun. 26, 2014

Related U.S. Application Data

(63) Continuation of application No. 13/262,795, filed as application No. PCT/EP2010/054550 on Apr. 6, 2010, now Pat. No. 8,663,260.

(30) Foreign Application Priority Data

Apr. 3, 2009    (GB) .................................... 0905748.0

(51) Int. Cl.
  *A61B 17/22*    (2006.01)
  *A61B 17/3207*    (2006.01)
  *A61B 17/32*    (2006.01)

(52) U.S. Cl.
  CPC ..... *A61B 17/3207* (2013.01); *A61B 17/320758* (2013.01); *A61B 2017/22054* (2013.01);
  (Continued)

(58) Field of Classification Search
  CPC ............. A61B 17/320758; A61B 2017/22067; A61B 2017/22079; A61B 2017/320766; A61B 2017/22068; A61B 2017/32006; A61B 2017/32004; A61B 2017/320733; A61B 2019/5278
  USPC ......... 606/159, 170, 127, 128, 167, 130, 180, 606/171, 194, 192, 193, 110–115, 191; 600/566, 567, 564, 113; 604/22, 604/101.01, 101.05, 154, 155, 35
  See application file for complete search history.

(56) References Cited

U.S. PATENT DOCUMENTS 1,431,416 A    10/1922    Parsons et al.
1,916,085 A    6/1933    Summers et al.
(Continued)

FOREIGN PATENT DOCUMENTS

EP    0820729    1/1998
EP    1820458    8/2007
(Continued)

OTHER PUBLICATIONS

Agnes Wittmann-Regis, Authorized Office, International Bureau of WIPO, International Preliminary Report of Patentability, International Application No. PCT/EP2010/054550, mailed Oct. 4, 2011, 7 pages.

*Primary Examiner* — Jocelin Tanner
(74) *Attorney, Agent, or Firm* — Fish & Richardson P.C.

(57) ABSTRACT

A rotational atherectomy device for removing a stenotic tissue from the iliac artery of a patient. The device comprises a flexible, rotatable drive shaft having an elongated proximal portion, an elongated distal portion. An abrasive element is mounted to the drive shaft between the elongated proximal and distal portions of the drive shad and between and spaced away from a pair of counterweights which are mounted to said elongated portions of the drive shaft. The eccentric abrasive element and the counterweights are configured for rapid rotation together with the drive shaft, the drive shaft is configured to extend throughout an entire length of the iliac artery to be treated. One elongated portion of the drive shaft extends out of the patient through a first access opening located in a femoral artery which is ipsilateral to the treated artery. Another elongated portion of the drive shaft extending through a second access opening located in another peripheral artery of the patient. A method of treating are iliac artery of a patient using such a rotational atherectomy device.

11 Claims, 9 Drawing Sheets

(52) U.S. Cl.
CPC .................. *A61B2017/22067* (2013.01); *A61B 2017/22079* (2013.01); *A61B 2017/320004* (2013.01); *A61B 2017/32006* (2013.01); *A61B 2017/320733* (2013.01); *A61B 2017/320766* (2013.01)

(56) References Cited

U.S. PATENT DOCUMENTS

| | | | |
|---|---|---|---|
| 4,784,636 A * | 11/1988 | Rydell | 604/22 |
| 4,931,635 A | 6/1990 | Toyama | |
| 4,990,134 A | 2/1991 | Auth et al. | |
| 5,250,060 A * | 10/1993 | Carbo et al. | 606/159 |
| 5,312,427 A * | 5/1994 | Shturman | 606/159 |
| 5,314,407 A | 5/1994 | Auth et al. | |
| 5,314,438 A | 5/1994 | Shturman | |
| 5,342,292 A | 8/1994 | Nita et al. | |
| 5,361,285 A | 11/1994 | Formanek et al. | |
| 5,370,653 A | 12/1994 | Cragg | |
| 5,584,843 A * | 12/1996 | Wulfman et al. | 606/159 |
| 5,681,336 A | 10/1997 | Clement et al. | |
| 5,730,717 A | 3/1998 | Gelbfish | |
| 5,868,708 A | 2/1999 | Hart et al. | |
| 6,010,533 A | 1/2000 | Pope et al. | |
| 6,132,444 A | 10/2000 | Shturman et al. | |
| 6,146,395 A | 11/2000 | Kanz et al. | |
| 6,241,706 B1 | 6/2001 | Leschinsky et al. | |
| 6,485,500 B1 | 11/2002 | Kokish et al. | |
| 6,565,588 B1 | 5/2003 | Clement et al. | |
| 6,685,718 B1 | 2/2004 | Wyzgala et al. | |
| 8,663,260 B2 | 3/2014 | Shturman | |
| 2002/0099367 A1 | 7/2002 | Guo et al. | |
| 2002/0138088 A1 | 9/2002 | Nash et al. | |
| 2004/0158270 A1 | 8/2004 | Wyzgala et al. | |
| 2008/0097498 A1 | 4/2008 | Shimizu et al. | |
| 2008/0319415 A1 | 12/2008 | Shturman | |
| 2009/0018564 A1 * | 1/2009 | Shturman | 606/159 |
| 2009/0069829 A1 | 3/2009 | Shturman | |
| 2009/0182359 A1 | 7/2009 | Shturman | |
| 2009/0312777 A1 | 12/2009 | Shturman | |
| 2009/0318942 A1 | 12/2009 | Shturman | |
| 2009/0326568 A1 | 12/2009 | Shturman | |
| 2010/0010522 A1 | 1/2010 | Shturman | |
| 2010/0049226 A1 | 2/2010 | Shturman | |
| 2012/0035633 A1 | 2/2012 | Shturman | |
| 2012/0109170 A1 | 5/2012 | Shturman et al. | |

FOREIGN PATENT DOCUMENTS

| | | |
|---|---|---|
| WO | WO 01/15759 | 3/2001 |
| WO | WO 2006/126176 | 11/2006 |

* cited by examiner

ROTATIONAL ATHERECTOMY DEVICE WITH ECCENTRIC ABRASIVE ELEMENT AND METHOD OF USE

CROSS-REFERENCE TO RELATED APPLICATIONS

This application is a continuation of U.S. application Ser. No. 13/262,795 filed on Oct. 21, 2011, which is a national phase application based on PCT/EP2010/054550 filed on Apr. 6, 2010, which claims priority of UK Patent Application No. 0905748.0 filed on Apr. 3, 2009. The contents of these previous applications are fully incorporated by herein by reference.

The present invention relates to a rotational atherectomy device for removing a stenotic lesion from within a vessel of a patient. More specifically, the invention relates to a rotational atherectomy device for removing or reducing a stenotic lesion in the iliac artery by rotating an abrasive element within the artery to partially or completely ablate the stenotic lesion and simultaneously remove out of the patient's body abraded particles (embolic particles or debris) released into the treated artery during the rotational atherectomy procedure. It should be understood that rotational atherectomy devices and rotational atherectomy procedures are often referred to as rotational angioplasty devices and rotational angioplasty procedures. One type of rotational atherectomy devices is referred to as an orbital atherectomy device. All these terms may be used interchangeably herein.

Atherosclerosis, the clogging of arteries, is a leading cause of coronary heart disease. Blood flow rough the peripheral arteries (e.g., carotid, femoral, renal, etc.), is similarly affected by the development of atherosclerotic blockages. One conventional method of removing or reducing blockages in blood vessels is known as rotational atherectomy. A device and a method for performing the Rotational Atherectomy Procedure are known from U.S. Pat. No. 4,990,134 to Auth. A rotational atherectomy (angioplasty) device based on this patent is commercially available from Boston Scientific Corporation of Natik, Mass., USA. The Auth device includes an abrasive burr which is attached to a distal end of a hollow flexible drive shaft. The abrasive surface of the burr is formed from diamond particles. The device is rotated around a special guidewire, which is advanced across the stenotic lesion. The device is advanced towards the stenotic lesion around (over) the guidewire. The abrasive burr is positioned against the occlusion and the drive shaft is rotated around the guidewire at extremely high speeds (e.g., 20,000-160,000 rpm). As the abrasive burr rotates, the physician repeatedly advances it towards the stenotic lesion so that the abrasive surface of the burr scrapes against the occluding tissue and disintegrates it, reducing the occlusion and improving the blood flow through the vessel. It should be understood that the terms abrasive burr and abrasive element may be used interchangeably herein.

U.S. Pat. No. 6,132,444 to Shturman (the instant inventor) et al., describes another rotational atherectomy device of the prior art. The Shturman device comprises an abrasive element located proximal to and spaced away from a distal end of the drive shaft. This abrasive element is formed from diamond particles directly electroplated to wire turns of an enlarged diameter portion of the drive shaft. The enlarged diameter portion of the drive shaft is asymmetric and is responsible for providing an abrasive element with a centre of mass which is spaced away from the rotational axis of the drive shaft. The device is rotated around a special guidewire and its eccentric abrasive element is able to open the treated stenotic lesion to a diameter substantially larger than the maximum diameter of the abrasive element.

U.S. Pat. No. 7,507,245 to Shturman (the instant inventor) et al., describes a third embodiment of the rotational atherectomy device of the prior art. The device of U.S. Pat. No. 7,507,245 is similar to the device of U.S. Pat. No. 6,132,444 except that the abrasive element comprises a prefabricated abrasive crown disposed around the eccentric enlarged diameter portion of the drive shaft. The device is commercially produced by Cardiovascular Systems, Inc. of St. Paul, Minn.

The Patent Application WO 2006/126176 to Shturman (the current inventor) describes a rotational atherectomy device comprising a solid eccentric abrasive element and two solid asymmetric support elements mounted on a hollow flexible drive shaft. The solid asymmetric support elements have their centres of spaced away (offset) from a rotational (longitudinal) axis of the drive shaft and, during rotation of the drive shaft, act as counterweights to the eccentric abrasive element. In the most preferred embodiment of the invention, the centre of mass of each of the solid counterweights is separated from the centre of mass of the abrasive element by an angle of 180 degrees around the axis of the drive shaft. When the drive shaft of the rotational atherectomy device with solid counterweights is rotated, centrifugal forces generated by the solid counterweights and the eccentric, abrasive element preferably act in substantially the same plane but in opposite directions. These centrifugal forces cause the distal end portion of the drive shaft to flex and assume a generally bowed or arcuate shape. During rotation of the drive shaft, the abrasive element and each of two solid counterweights move in orbital fashions around the axis of rotation of the drive shall in orbits that are substantially larger than the respective diameters of the abrasive element or solid counterweights.

Disadvantages associated with either limited or completely absent distal embolic protection of all commercially available rotational atherectomy devices have been addressed in WO 2006/126076 to Shturman (the instant inventor). An accordance with WO 2006/126076 drive shaft has a fluid impermeable wall and allows an antegrade flow of pressurised fluid through a lumen of the drive shaft from a proximal end towards a distal end of the drive shaft. A portion of the pressurised fluid, after entering the treated vessel distal to the abrasive element, flows in a retrograde direction around the abrasive element and across the treated stenotic lesion to entrain abraded embolic particles and evacuate them from the treated vessel as soon as they have been abraded by the abrasive element of the device. Several other embodiments of the device with distal embolic protection capability are disclosed in WO 2008/006701, WO 2008/006705, WO 2008/006706, WO 2008/006708, and WO 2008/062069 to Shturman (the instant inventor), but in every one of these embodiments the abraded particles are entrained and evacuated front the patient's body by fluid which flows around the abrasive element in the retrograde direction (i.e. against the direction of the flow of blood in the treated artery).

Over the last few years Edwards Lifesciences Corp. and CoreValve, Inc. (both of Irvine, Calif.) introduced to the market and clinical trials respectfully two types of novel Aortic Heart Valves which are configured for Transcatheter Aortic Valve Replacement. A delivery catheter for transfemoral placement of Edwards SAPIEN Heart Valve has an outer diameter of about 7 millimeters. The Delivery Catheter which is used during the CoreValve ReValving® percutaneous aortic valve replacement procedure has an outer diameter of about 6 millimeters. The delivery catheters of both companies have to be advanced though the Iliac Artery of the patient. A large number of patients who may benefit from the Transcatheter Aortic Valve Replacement have atherosclerotic occlusions in their Iliac Arteries. Often Iliac Arteries of older patients are not only affected by calcified atherosclerotic lesions but are tortuous as well. Therefore what is needed is a rotational atherectomy device which will be able to partially or completely ablate both the soft and calcified stenotic lesions in the tortuous iliac arteries of older patients.

It is the objective of this invention to provide a rotational (orbital) atherectomy device which can ablate atherosclerotic plaques in tortuous iliac arteries and simultaneously remove abraded particles out of the patient's body.

It is another objective of this invention to provide a rotational (orbital) atherectomy device which not only can simultaneously ablate the plaque and remove abraded particles out of the patient, but which can remove abraded particles from the iliac artery without the need to form the retrograde flow of fluid around the abrasive element of the device.

All rotational (orbital) atherectomy devices described above have an abrasive element which is moved back and forth across the stenotic lesion by alternately pulling and pushing on the elongated drive shaft of the device. Pushing on the proximal end of the elongated drive shaft, after removing the guidewire, may cause the flexible drive shaft to bend within the elongated drive shaft sheath. This, in turn, may cause discrepancy between the forward movement of the turbine (the drive shaft is connected to the turbine) and the forward movement of the abrasive element. Therefore, it is yet another objective of this invention to eliminate such a discrepancy by provide a rotational (orbital) atherectomy device in which the abrasive element is moved back and forth across the stenotic lesion by alternately pulling one end of the drive shaft in one direction and the other end of the drive shaft in the opposite direction.

According to a preferred embodiment of the invention, the rotational atherectomy device for removing a stenotic tissue from the iliac artery of a patient is comprising a flexible, rotatable drive shaft having an elongated proximal portion, an elongated distal portion, and an abrasive element mounted to the drive shaft between the elongated proximal and distal portions of the drive shaft and between and spaced away from a pair of counterweights which are mounted to said elongated portions of the drive shaft, the eccentric abrasive element and the counterweights being configured for rapid rotation together with the drive shaft, the drive shaft being configured for extending throughout an entire length of the iliac artery to be treated and having one elongated portion of the drive shaft extending out of the patent through a first access opening located in a femoral artery which is ipsilateral to the treated artery, and the other elongated portion of the drive shaft extending through a second access opening located in another peripheral artery of the patient.

Preferably, the device includes a pair of elongated drive shaft sheaths, one drive shaft sheath configured for slidably receiving the elongated proximal portion of the drive shaft and the other drive shaft sheath configured for slidably receiving the elongated distal portion of the drive shaft, the drive shaft sheaths having distal ends and being configured for advancement around corresponding portions of the drive shaft into the treated iliac artery such that the distal ends of the sheaths become positioned spaced away from the counterweights, the space between the distal ends of the drive shaft sheaths allowing to repeatedly move the rotating abrasive element back and forth along the treated iliac artery and abrade the stenotic lesion.

Preferably, one of the drive shaft sheaths should be in a fluid communication with a source of pressurized fluid, said pressurized fluid flows into the treated artery through said one drive shaft sheath, entrains abraded embolic particles, and is drained out from the treated artery through the other drive shaft sheath.

Preferably, an inflatable occlusion balloon should be mounted to the distal drive shaft sheath, the inflatable occlusion balloon being configured, when inflated, to restrict the flow fluids and abraded particles from the treated stenotic lesion into the femoral artery.

Preferably, at least one of the elongated portions of the drive shaft is configured to be connected to a rotatable shaft of a prime mover, the prime mover being configured for rotating the drive shaft.

Preferably, the prime mover is slidably received within a housing of an advancer mechanism so that an operator can alternately pull and push on the elongated portion of the drive shaft by moving the prime mover back and forth within the housing of the advancer mechanism.

Preferably, the elongated distal portion of the drive shaft is configured to be connected to a rotatable shaft of a prime mover, the prime mover being configured for rotating the drive shaft.

Preferably, the prime mover is slidably received within a housing of an advancer mechanism so that an operator can alternately pull and push on the elongated distal portion of the drive shaft by moving the prime mover back and forth within the housing of the advancer mechanism.

Preferably, the elongated proximal portion of the drive shaft is configured to be connected to rotatable shaft of a prime mover, the prime mover being configured for rotating the shaft.

Preferably, the prime mover is slidably received within a housing of an advancer mechanism so that an operator can alternately pull and push on the elongated proximal portion of the drive shaft by moving the prime mover back and forth within the housing of the advancer mechanism.

Preferably, the device includes a pair of prime movers and each of the elongated portions of the drive shaft is configured to be connected to a rotatable shaft of one of the two prime movers, the prime movers being configured for rotating the drive shaft.

Preferably, each of the prime movers is slidably received within a housing of an advancer mechanism so that an operator can alternately pull on distal and proximal portions of the drive shaft by alternately moving the prime movers away from distal ends of the housings of the advancer mechanisms.

Preferably, proximal ends of both elongated portions of the drive shaft are configured for releasable connection to opposite ends of a rotatable shaft of a prime mover which is configured for rotating the drive shaft.

Preferably, the prime mover is slidably received within a housing of an advancer mechanism so that an operator can alternately pull on distal and proximal portions of the drive shaft by moving the prime mover back and forth within the housing of the advancer mechanism.

Preferably, the device includes a prime mover for rotating the drive shaft and an advancer mechanism which is configured for slidably carrying the prime mover.

Preferably, one of the elongated portions of the drive shaft is configured to be connected to a rotatable shaft of the prime mover, and the drive shaft sheath extending around said portion of the shaft is configured to be connected to a housing of the advancer mechanism so that an operator can repeatedly move the abrasive element back and forth across the stenotic lesion by moving the prime mover back and forth with respect to the housing of the advancer mechanism.

Preferably, the atherectomy device comprises a pair of advancer mechanisms, a first advancer mechanism having a first housing which slidably carries a prime mover configured for rotating the drive shaft, and a second advancer mechanism having a second housing which slidably carries a hollow body comprising a rotatable shaft supported by at least one bearing which is disposed within the hollow body, and wherein one of the two elongated portions of the drive shaft is configured to be connected to a rotatable shaft of the prime mover, and the other of the two elongated portions of the drive shaft being configured to be connected to the rotatable drive shaft of the second advancer mechanism, and further wherein the drive shaft sheaths are configured to be connected to distal ends of the housings of the advancer mechanisms so that an operator can move the abrasive element across the stenotic lesion by alternately moving the prime mover and the hollow body away from the distal ends of the housings of the first and second advancer mechanisms.

Preferably, the device comprising a flexible, rotatable drive shaft having an elongated proximal portion, an elongated distal portion, and an abrasive element mounted to the drive shaft between the elongated proximal and distal portions of the drive shaft and between and spaced away from a pair of counterweights which are mounted to said elongated portions of the drive shaft, the eccentric abrasive element and the counterweights being configured for rapid rotation together with the drive shaft, the drive shaft being configured for extending throughout an entire length of the artery to be treated and having one elongated portion of the drive shaft extending out of the patient through a first access opening located in a femoral artery, and the other elongated portion of the drive shaft extending through a second access opening located in another peripheral artery of the patient.

Preferably, the device includes a pair of elongated drive shaft sheaths, one drive shaft sheath configured for slidably receiving the elongated proximal portion of the drive shaft and the other drive shaft sheath configured for slidably receiving the elongated distal portion of the drive shaft, the drive shaft sheaths having distal ends and being configured for advancement around corresponding portions of the drive shaft into the treated artery such that the distal ends of the sheaths become positioned spaced away from the counterweighs, the space between the distal ends of the drive shaft sheaths allowing to repeatedly move the rotating abrasive element back and forth along the treated artery and abrade the stenotic lesion.

Preferably, one of the drive shaft sheaths is in a fluid communication with a source of pressurized fluid, said pressurized fluid flows into the treated artery through said one drive shaft sheath, entrains abraded embolic particles, and is drained out from the treated artery through the other drive shaft sheath.

Preferably, the device includes a prime mover for rotating the drive shaft.

Preferably, the prime mover is slidably received within a housing of an advancer mechanism so that an operator can repeatedly move the abrasive element back and forth across the stenotic lesion by repeatedly moving the prime mover back and forth within the housing of the advancer mechanism.

Preferably, the device includes an advancer mechanism which is configured for repeatedly moving the rotating prime mover together with the rotating drive shaft and the abrasive element back and forth across the treated stenotic lesion.

Preferably, the elongated drive shaft sheath which is used for draining fluid should include a separate drainage lumen which should be configured exclusively for draining fluid and abraded particles out from the treated artery.

Preferably, the elongated distal drive shaft sheath includes an occlusion balloon inflation lumen.

Preferably, the centre of mass of the eccentric abrasive element and the centres of mass of the counterweights are spaced in opposite directions with respect to the longitudinal axis of the drive shaft.

Preferably, each of the two elongated portions of the drive shaft is at least 15 centimeters long.

Preferably, each of the two elongated portions of the drive shaft is at least 30 centimeters long.

Preferably, an ultrasound transducer is mounted near the distal end of one of the drive shaft sheaths, the ultrasound transducer allowing acquisition of transverse ultrasound images of the treated artery.

Preferably, the second access opening is located in a femoral artery which is contralateral with respect to the iliac artery to be treated.

Alternatively, the second access opening may be located in an artery of the upper extremity of the patient.

According to the alternative embodiment, the second access opening may be located in one of the radial arteries of the patient.

BRIEF DESCRIPTION OF DRAWINGS

FIG. 1 is a side sectional view of iliac arteries. A stenotic lesion to be treated is located in the right iliac artery. A drive shaft of an atherectomy device of the invention is extending through the iliac arteries. FIG. 1 shows that an eccentric abrasive element is mounted to the drive shaft between and spaced away from a pair of counterweights which are mounted to the elongated portions of the drive shaft. FIG. 1 shows that one elongated portion of the drive shaft (i.e. distal) extends out of the patient through a first access opening located in the ipsilateral to the lesion femoral artery of the patient and the other elongated portion of the drive shaft (i.e. proximal) extends out of the patient through a second access opening located in the contralateral to the lesion femoral artery of the patient;

FIG. 2 is a side sectional view which shows that one elongated drive shaft sheath has been advanced over the elongate proximal portion of the drive shaft, and another elongated drive shaft sheath has been advanced over the elongate distal portion of the drive shaft. FIG. 2 shows that distal ends of the sheaths are spaced away from the counterweights. FIG. 2 shows an occlusion balloon which are mounted to the distal drive shaft sheath near the distal end of the sheath. FIG. 2 shows that the elongated portion on the drive shaft on each side of the abrasive element is connected to the advancer mechanism. This allows moving the abrasive element in one direction across the stenotic lesion by pulling on the elongated portion of the drive located on one side of the abrasive element, and moving the abrasive element in the opposite direction by pulling on the elongated portion of the drive, located on the other side of the abrasive element. FIG. 2 shows that the elongated proximal drive shaft sheath has been connected to a source of pressurized fluid (not shown). FIG. 2 illustrates that pressurized fluid flows towards the treated iliac artery through the proximal drive shaft sheath and is drained from the artery through the distal drive shaft sheath.

FIGS. 4 and 5 are side sectional views illustrating the process of ablation of the atherosclerotic plaque by the rotating abrasive element which is repetitively moved back and forth across the stenotic lesion. FIGS. 4 and 5 illustrate that moving the abrasive element in one direction across the stenotic lesion is achieved by moving a first turbine away from the distal end of the housing of a first advancer mechanism, and moving the abrasive element in the opposite direction is achieved by moving the second turbine away from the distal end of the housing of the second advancer mechanism. FIGS. 4 and 5 illustrate that abraded particles are removed from the patient as soon as they are produced;

Reference is made in this specification to the "distal" and "proximal" ends of the elongated drive shaft sheaths. For the purpose of this specification, the distal end is considered to refer to the end of the sheath which is located inside the patient's body, and the proximal end is considered to refer to that end of the sheath which is located outside the patient's body. Embolic particles are indicated by symbol "EP", and the flow of fluid through the device is indicated by arrows "F". It should be noted that the terms "guidewire" and "guide wire" are used interchangeably to the medical device literature. The terms "prime mover" and "gas turbine" are used interchangeably throughout this specification as well. It should be understood that any connection of the elongated portion of the drive shaft to a shaft of the prime mover can be made a releasable connection. It should be also understood that any connection of the drive shaft sheath to a housing of an advancer mechanism can be made a releasable connection.

Operation of the rotational atherectomy device to abrade the stenotic lesion located in the iliac artery will now be described with reference to FIGS. 1 to 8 of the accompanying drawings.

Figure 1:
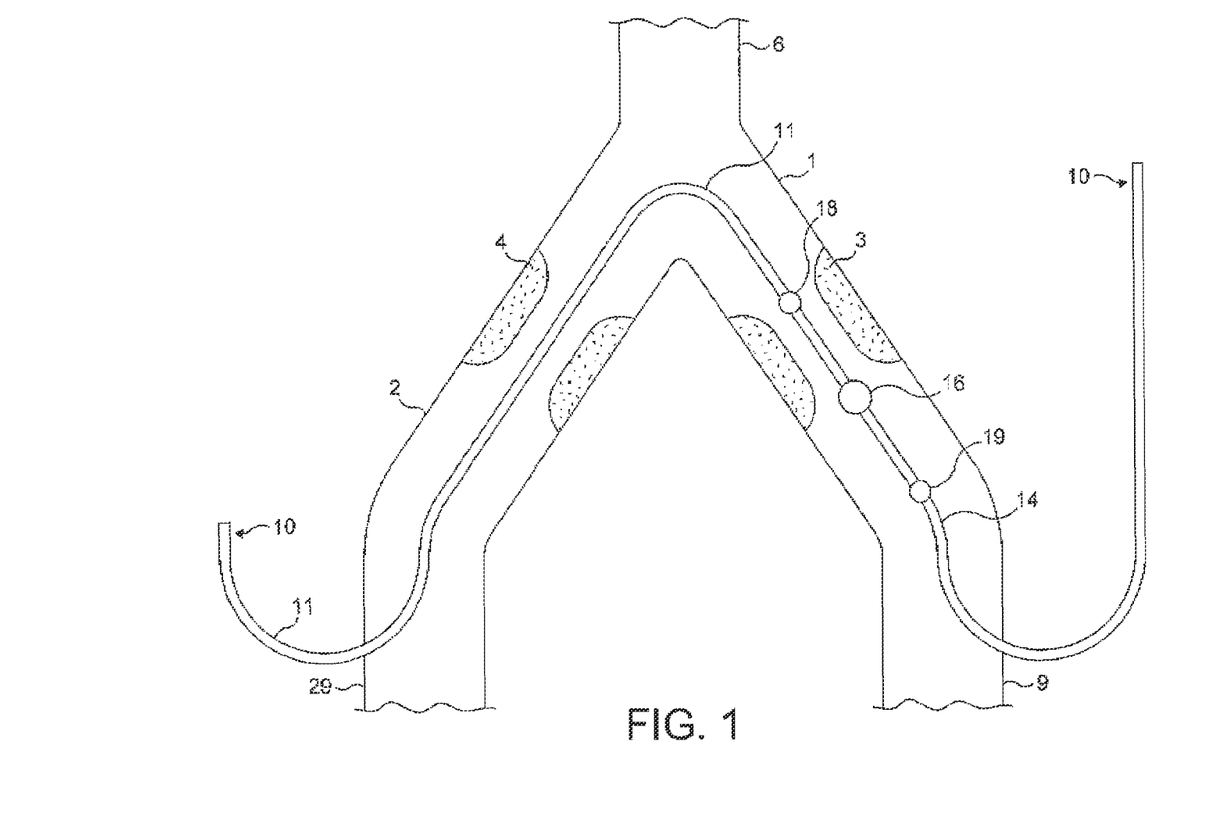

FIG. 1 is a side sectional view of iliac arteries. A stenotic lesion 3 to be treated is located in the right iliac artery 1. A drive shaft 10 of an atherectomy device of the invention is extending through the iliac arteries. FIG. 1 shows that an eccentric abrasive element 16 is mounted to the drive shaft 10 between and spaced away from pair of counterweights 18, 19 which are mounted to elongated portions of the drive shaft 11, 14. FIG. 1 shows that one elongated portion or the drive shaft (i.e. distal) 14 extends out of the patient through a first access opening located in the ipsilateral to the lesion femoral artery 9 of the patient and the other elongated portion of the drive shaft (i.e. proximal) extends out of the patient through a second access opening located in the contralateral to the lesion femoral artery 29 of the patient. It should be understood that one of the of elongated portions of the drive shaft 11, 14 may be shorter than the other, but even the shorter elongated portion of the drive shaft should have at least 10 centimeters in its length. Preferably, each elongated portion of the drive shaft should have at least 30 centimeters in its length.

It should be noted that the drive shaft 10 may be advanced into its position over the guidewire (not shown). The guidewire may be introduced, for example, from the contralateral side through a percutaneous puncture, and advanced superiorly towards the aorta 6. A retrieval catheter (not shown) is introduced through a vascular access site in the ipsilateral femoral artery and advanced into the ipsilateral iliac artery. The retrieval catheter is used to grasp the guidewire and retract it inferiorly through the ipsilateral vascular access site. The above described technique of advancing the guidewire is well known to the interventional cardiologists and interventional radiologists. The guidewire is removed after the drive shaft 10 has been advanced over it.

Figure 2:
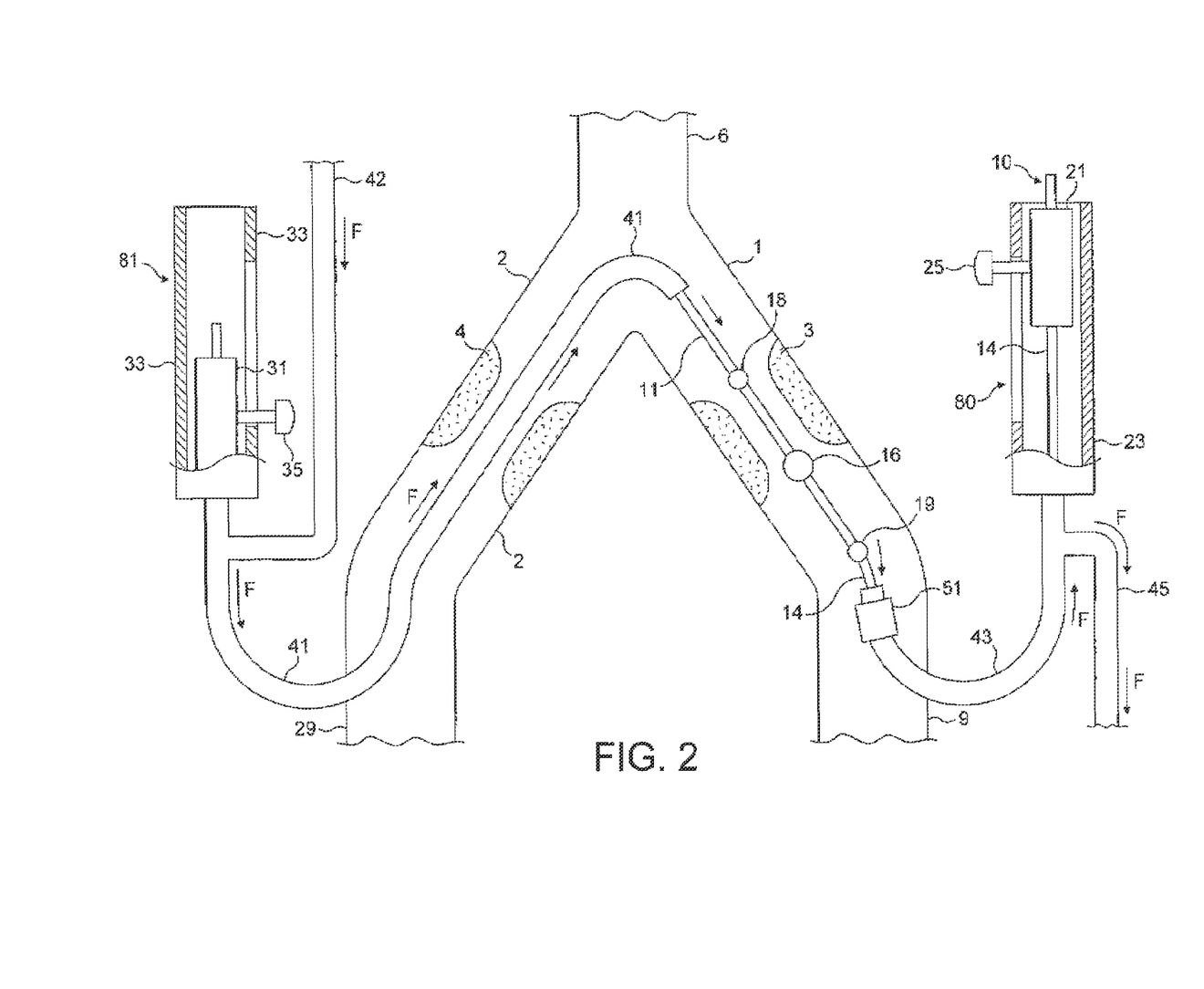

FIG. 2 is a side sectional view which shows that one elongated drive shaft sheath 41 has been advanced over the elongate proximal portion 11 of the drive shaft 10, and another elongated drive shaft sheath 43 has been advanced over the elongate distal portion 14 of the drive shaft 10. The elongated drive shaft sheaths 41, 43 are configured for slidably receiving corresponding portions of the drive shaft 10. FIG. 2 shows that the distal ends of the sheaths 41, 43 are spaced away from the counterweights 18, 19. The space between the distal ends of the elongated sheaths 41, 43 allows moving the rotating abrasive element 16 together with counterweights 18, 19 back and forth along the treated stenotic lesion 3 in the iliac artery 1. FIG. 2 shows that the elongated distal portion 14 of the drive shaft 10 has been connected to a prime mover 21 and the corresponding elongated drive shaft sheath 43 has been connected to a housing 23 of an advancer mechanism 80 which carries the prime mover (i.e. gas turbine) 21. The prime mover 21 is configured for rotating the drive shaft 10. The advancer mechanism 80 slidably receives the prime mover 21 within its housing 23 and allows moving the rotating drive shaft 10 and its abrasive element back and forth across the stenotic lesion to be treated, it should be noted that the prime mover 21 usually includes a gas turbine, but it may be comprised from an electric motor as well.

FIG. 2 shows that the elongated proximal drive shaft sheath 41 has to be been connected, for example, via a tube 42 to a source of pressurised fluid (not shown). FIG. 2 illustrates that pressurized fluid flows towards the treated iliac artery 1 through the proximal drive shaft sheath 41 and is drained from the artery through the elongated distal drive shaft sheath 43 and its side branch 45. The direction of the flow of pressurized fluid is indicated by arrows "F". It should be noted that a power injector or any other suitable pump may be used for pumping fluid into the elongated proximal drive shaft sheath 41.

Figure 3:
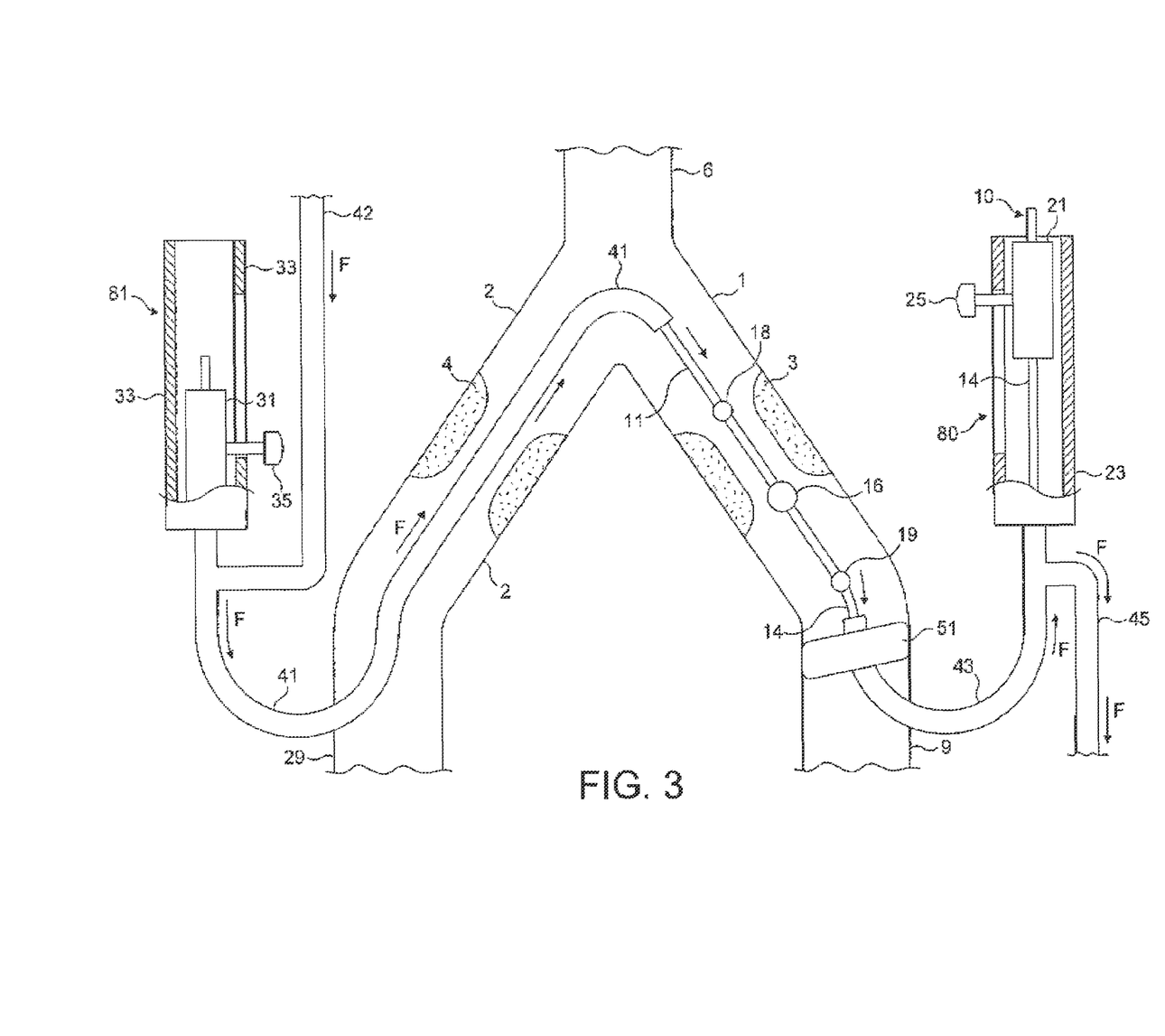
FIG. 3 shows that the inflated occlusion balloon prevents the flow of blood from the treated stenotic artery into the femoral artery. The occlusion balloon is mounted to the distal drive shaft sheath near the distal end of the sheath.

FIG. 3 illustrates that occlusion balloon 51 has been inflated within the treated vessel 1. The occlusion balloons 51 is mounted to the elongated distal drive shaft sheath 43 near the distal end of the sheath. The occlusion balloons 51 prevents the flow of blood and abraded particles away from the treated stenotic lesion 3 into the femoral artery 9.

It should be understood that repeated back and forth movements of the rotating abrasive element 16 along treated iliac artery 1 and across the stenotic lesion 3 can be achieved by repeatedly moving back and forth the turbine 21 within the housing 23 of the advancer mechanism 80. It should be noted that the back moving turbine 21 pulls the elongated distal portion 14 of the shaft 10, and the forward moving turbine 21 pushes on the proximal end of the elongated distal portion 14 of the shaft 10. As it was already described, in the preferred embodiment of the invention, the guidewire is used only to advance the drive shaft 10 through the iliac arteries. Pushing on the proximal end of the elongated drive shaft, after removing the guidewire, may cause the flexible drive shaft to bend within the elongated drive shaft sheath 43. This, in turn, may cause discrepancy between the forward movement of the turbine 21 and the forward (proximal) movement of the abrasive element 16. An embodiment shown in FIGS. 3 through 6 is addressing this issue by providing a second advancer mechanisms 81 and moving the abrasive element 16 proximally across the treated stenotic lesion 3 by pulling the elongated proximal portion 11 of the drive shaft 10 by the second turbine 31 instead of pushing on the proximal end of the elongated distal portion 14 of the drive shaft 10 by the turbine 21. The physician is moving the abrasive element 16 in one direction across the stenotic lesion 3 by pulling the proximal end of the elongated portion of the drive shaft located on one side of the abrasive element 16, and the physician is moving the abrasive element 16 in the opposite direction by pulling the proximal end of the elongated portion of the drive located on the other side of the abrasive element 16. It should be noted that the second advancer mechanism 81 does not need to have a compete turbine assembly and the housing 31 may include only one or two bearings for rotatably supporting the proximal end of the shaft 10.

Figure 4:
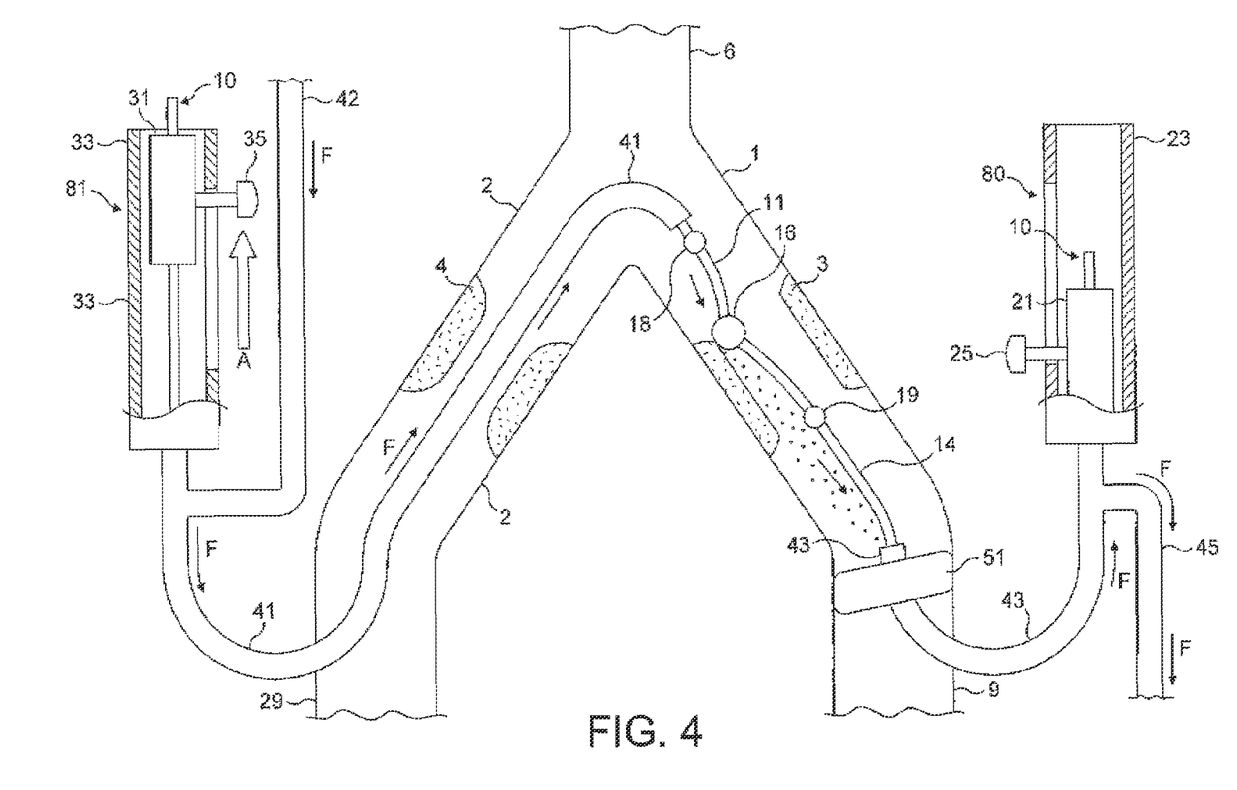

FIG. 4 shows that rotation of the eccentric abrasive element 16 and counterweights 18, 19 has been initiated. The abrasive element 16 is orbiting within the stenotic lesion and abrading it. FIG. 4 illustrates that abraded particles "EP" are entrained by the flow of and they are removed from the treated iliac artery 1 and the patient's body as soon as they are produced.

Figure 5:
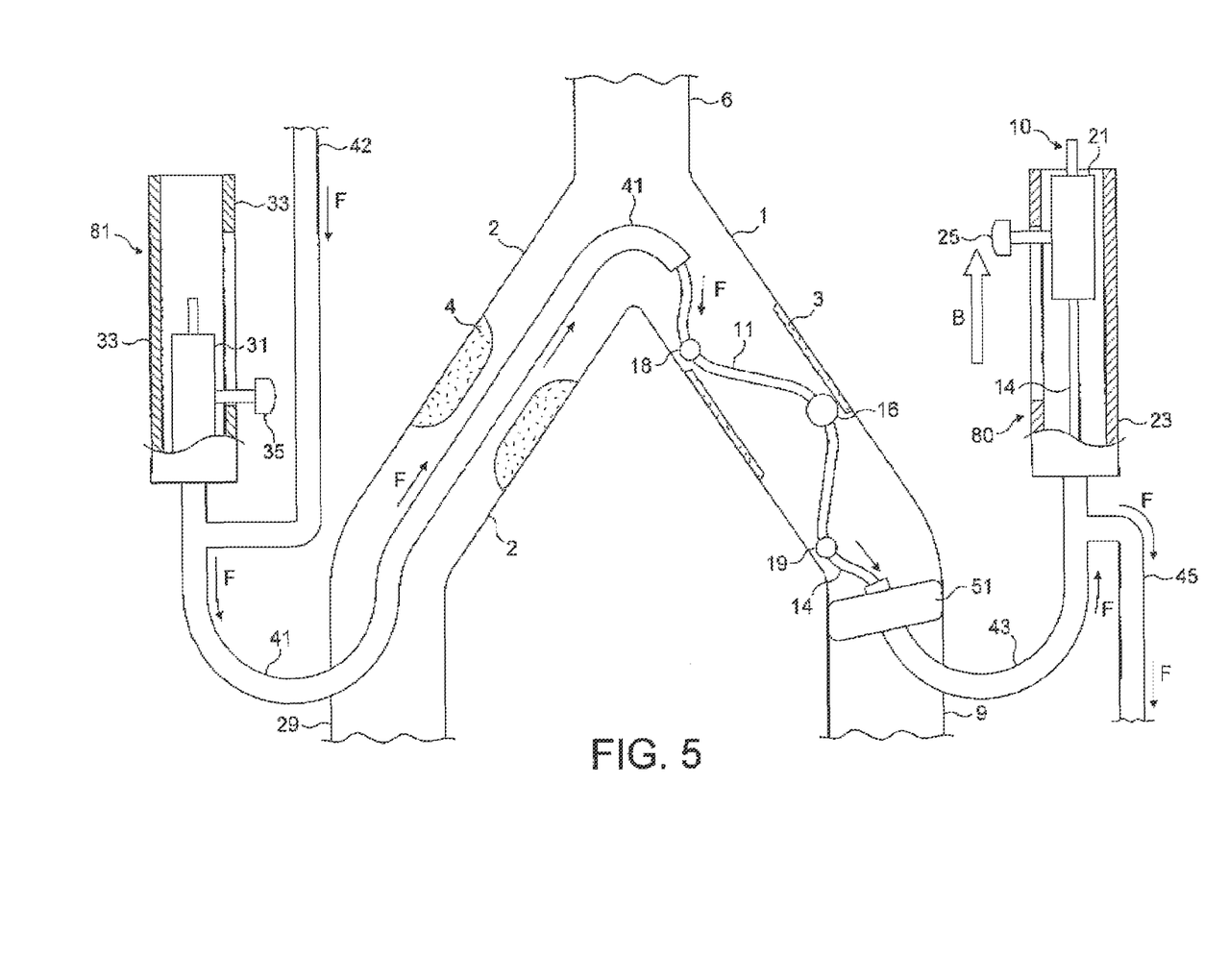

FIGS. 4 and 5 illustrate back and forth movements of the rotating abrasive element 16 along the treated iliac artery 1 and across the stenotic lesion 3. A physician can repeatedly move the rotating abrasive element 16 back and forth by repeatedly moving back and forth the turbine 21 (knob 25) within the housing 23 of the advancer mechanism 80.

Figure 6:
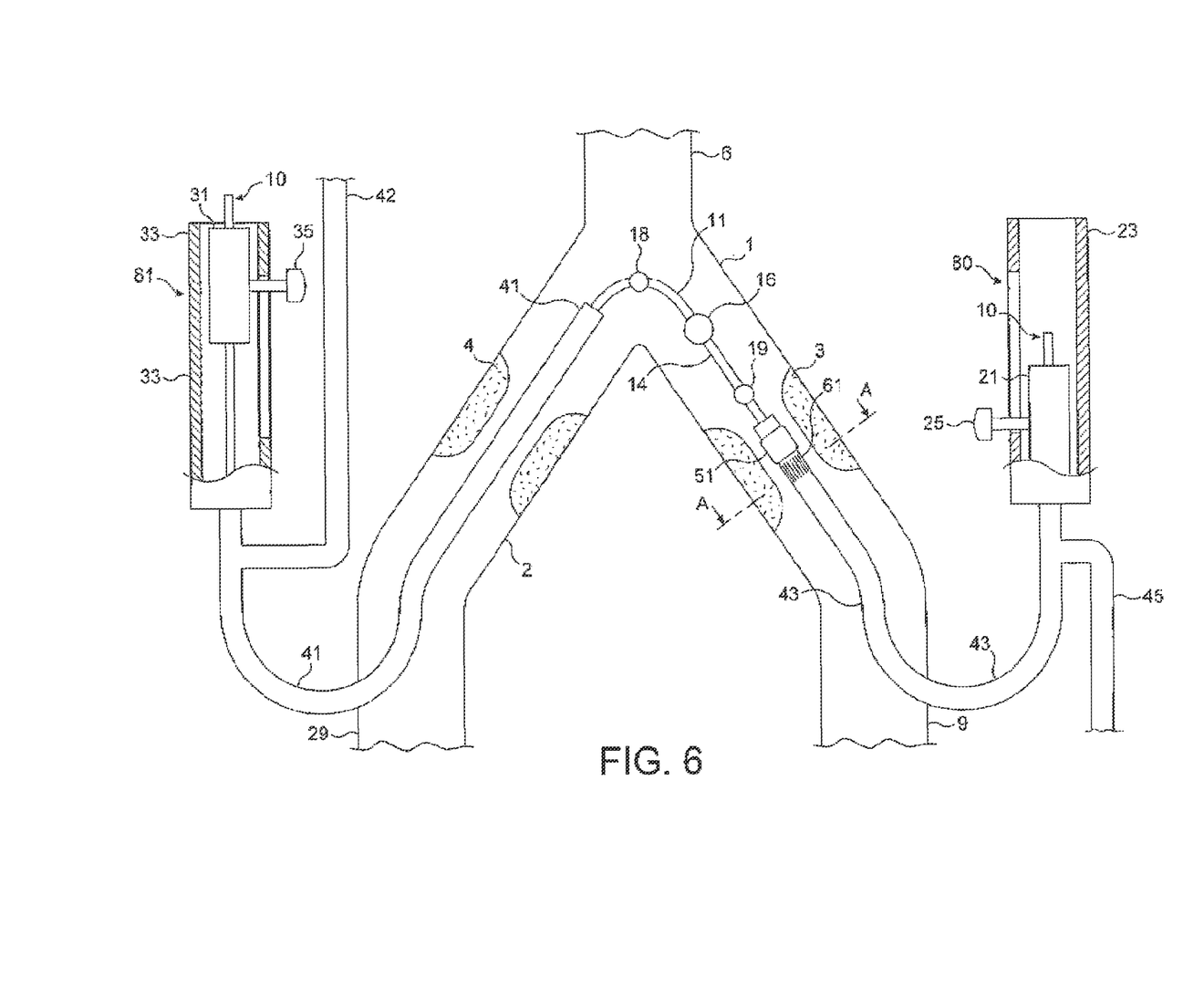
FIG. 6 is a side sectional view illustrating that a plurality of ultrasound transducers can be mounted to a distal end portion of one of the elongated drive shaft sheaths. These transducers allow repeatedly acquiring cross-sectional ultrasound images of the treated vessel throughout the atherectomy procedure.
Figure 6A:
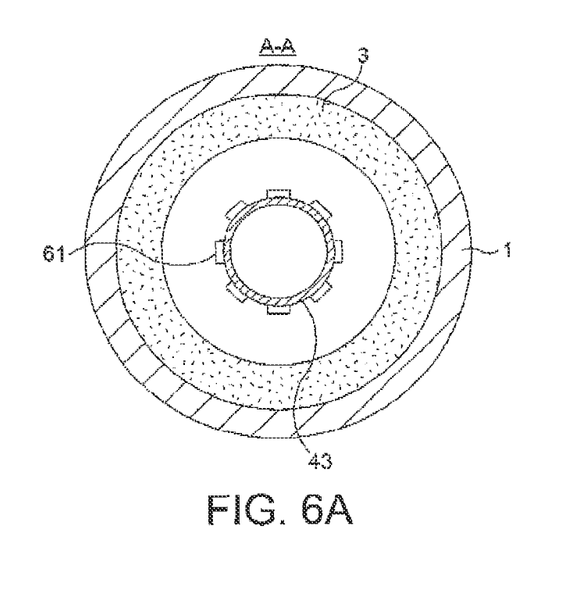
FIG. 6A is a cross-sectional view taken along the line A-A shown in FIG. 6 and shows an ultrasound image acquired by the ultrasound transducers.

FIG. 6 illustrates that a plurality of ultrasound transducers 61 can be mounted to a distal end portion of the elongated distal drive shaft sheath 43. These transducers 61 allow repeatedly acquiring cross-sectional ultrasound image(s) of the treated vessel throughout the atherectomy procedure and enhancing its safety. FIG. 6A is a cross-sectional view taken along the line A-A shown in FIG. 6 and shows an ultrasound image acquired by the ultrasound transducers 61.

Figure 7:
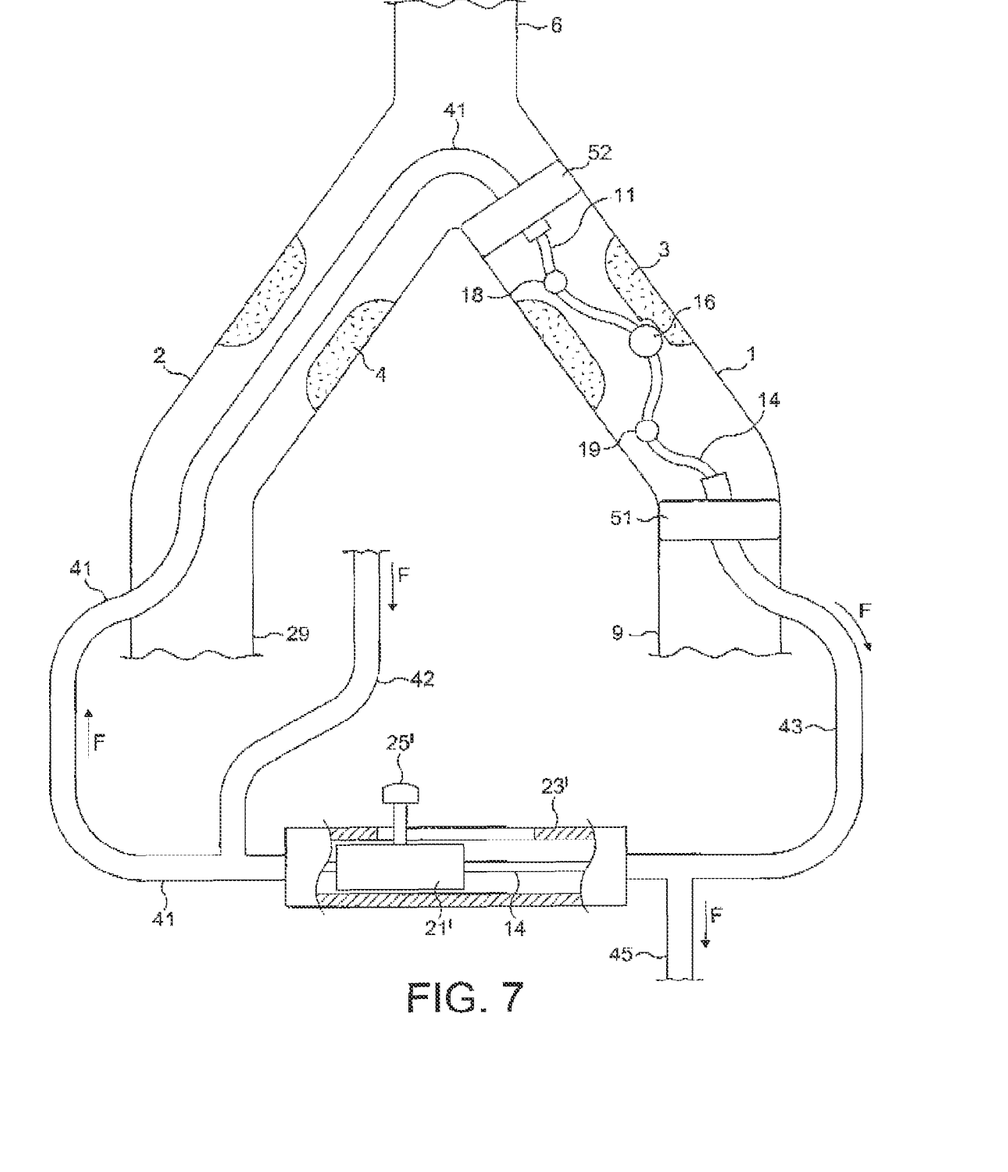
FIG. 7 is a side sectional view showing that proximal ends of the elongated portions of the drive shaft can be connected to the opposite ends of the same turbine shaft. This allows moving the abrasive element back and forth across the stenotic lesion by moving the turbine back and forth with respect to the housing of the advancer mechanism.
Figure 8:
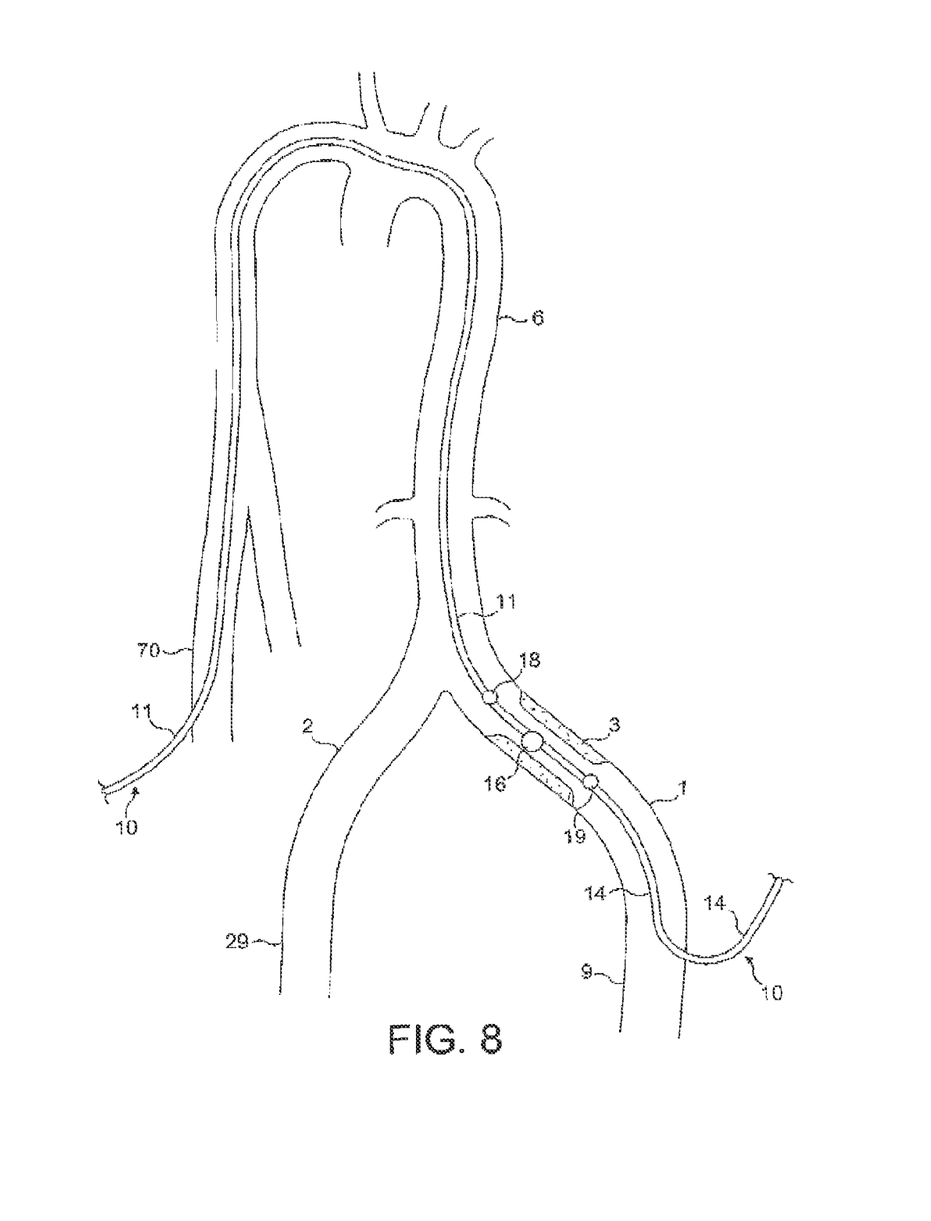
FIG. 8 is a side sectional view illustrating that one elongated portion of the drive shaft (i.e. distal) extends out of the patient through a first access opening located in the ipsilateral to the treated iliac artery femoral artery of the patient and the other elongated portion of the drive shaft (i.e. proximal) extends out of the patient through a second access opening located in the radial artery of the patient.

FIG. 7 is a side sectional view showing that proximal ends of the elongated distal and proximal portions of the drive shaft 10 (i.e. elongated portions located on opposite sides of the abrasive element 16) can be connected to the opposite ends of the shaft of the single turbine 23'. This allows moving the abrasive element 16 back and forth across the stenotic lesion 3 by moving back and forth the single turbine 21' with respect to the housing 23' of the advancer mechanism.

It should be noted that after completing the treatment of one iliac artery (i.e. right) the abrasive element 16 can be repositioned into another stenotic iliac artery (i.e. left) without removing the drive shaft 10 out of the patient's body.

FIG. 3 is a side sectional view illustrating that one elongated portion of the drive shaft (i.e. distal portion 14) may extend out of the patient through a first access opening located in the ipsilateral with respect to the stenotic lesion femoral artery 9 and the other elongated portion of the drive shaft (i.e. proximal portion 11) may extend out of the patient through a second access opening located in the radial artery 70 instead of extending through the access opening in the contralateral femoral artery 29.

It should be noted that radio opaque markers (rings) mounted to the drive shaft sheaths in order to facilitate appropriate positioning of the sheaths with respect to the counterweights 18, 19.

A preferred method of using the rotational (orbital) atherectomy device of the invention for treating, a stenotic lesion in the iliac artery should include the following steps:

a) positioning the drive shaft in the iliac arteries such that one elongated portion of the drive shaft extends out of the patient through a first access opening located in the femoral artery which is ipsilateral to the iliac artery to be treated, and the other elongated portion the drive shaft extends through a second access opening located in the femoral artery which is contralateral to the iliac artery to be treated;

b) positioning the abrasive element within the stenotic lesion to be treated and locating the drive shaft sheaths in the treated iliac artery such that their distal ends are spaced away from the counterweights abrasive;

c) inflating occlusion balloons of the distal sheaths;

d) initiating the flow of pressurized fluid through the first sheath and draining it through the second sheath; and e) initialing rotation of the drive shaft and repeatedly moving the rotating abrasive element back and forth across the treated stenotic lesion;

f) deflating occlusion balloons, repositioning the abrasive element and the a shaft sheaths along the treated artery, and repeating the steps b, c, d and e; and g) if the other iliac artery also has a stenotic lesion, then repositioning, the abrasive element in the other iliac artery, positioning the drive shaft sheaths in the treated artery such that their distal ends are spaced away from the abrasive element, and repeating the steps b, d, e, and f.

While the present invention is described herein in terms of certain preferred embodiments, those skilled in the art will recognize that various modifications and improvements may be made to the invention without departing from the scope thereof. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of the embodiments.

The invention claimed is:

1. A method of treating an iliac artery of a patient, comprising:

positioning an elongate catheter of a system for performing rotational atherectomy in a blood vessel of a patient, the elongate catheter defining a first lumen and a second lumen, the elongate catheter including an inflatable balloon member attached to and surrounding an outer diameter of an end portion of the elongate catheter, the balloon member in fluid communication with the first lumen, the balloon member configured to contact a blood vessel wall when the balloon member is in an inflated configuration;

rotating a rotational atherectomy device of the system while the rotational atherectomy device is at least partially disposed within the second lumen of the elongate catheter, the rotational atherectomy device comprising an elongate flexible drive shaft defining a central lumen and a longitudinal axis, the drive shaft configured for rotation about the longitudinal axis, an eccentric abrasive element that is mounted to the drive shaft such that a center of mass of the abrasive element is offset from the longitudinal axis of the drive shaft, and a pair of stability elements including a first stability element that is fixed to the drive shaft at a location proximal to the abrasive element, and a second stability element that is fixed to the drive shaft at a location distal to the abrasive element, wherein a distal portion of the drive shaft extends distally of a distal end of the second stability element, wherein said rotating the rotational atherectomy device is caused by a prime mover for rotating the drive shaft; and repeatedly moving the rotating drive shaft and its abrasive element back and forth across a stenotic lesion to remove stenotic lesion material from the blood vessel, wherein the abrasive element abrades the stenotic lesion material from the blood vessel.

2. The method of claim 1, further comprising locating the elongate catheter in the blood vessel such that a distal end of the elongate catheter is spaced away from the first stability element.

3. The method of claim 1, wherein the first stability element is a first counterweight, and the second stability element is a second counterweight.

4. The method of claim 3, further comprising inflating the inflatable balloon member and aspirating stenotic lesion material through the second lumen of the elongate catheter.

5. The method of claim 4, further comprising:
deflating the inflatable balloon member;
repositioning the drive shaft within the blood vessel; and
repeating the steps of rotating the rotational atherectomy device and repeatedly moving the rotating drive shaft and its abrasive element back and forth across the stenotic lesion.

6. The method of claim 1, further comprising:
advancing an intravascular ultrasound imaging catheter over the drive shaft into the blood vessel and across the stenotic lesion, and
acquiring cross-sectional images of the stenotic lesion area.

7. The method of claim 1, wherein the distal portion of the drive shaft that extends distally of the second stability element has a length that is greater than an axial length of the second stability element.

8. The method of claim 7, wherein the distal portion of the drive shaft extends at least 10 centimeters.

9. The method of claim 1, wherein the first and second stability elements are equally spaced apart from the abrasive element.

10. The system of claim 1, further comprising advancing the rotational atherectomy device over a guidewire and toward the stenotic lesion material, the guidewire being configured to be slidably disposed within the central lumen of the drive shaft.

11. The method of claim 1, wherein the elongate catheter operates as an elongate drainage catheter.

\* \* \* \* \*

UNITED STATES PATENT AND TRADEMARK OFFICE
CERTIFICATE OF CORRECTION

PATENT NO. : 9,089,362 B2  
APPLICATION NO. : 14/170923  
DATED : July 28, 2015  
INVENTOR(S) : Leonid Shturman It is certified that error appears in the above-identified patent and that said Letters Patent is hereby corrected as shown below:

Tile Page,

Column 2 Item (57) (Abstract) Line 6 Delete "shad" and insert --shaft--, therefor.

Column 2 Item (57) (Abstract) Line 17 Delete "are" and insert --an--, therefor.

In the Claims,

Column 12 Line 21 Claim 10 Delete "system of claim 1" and insert --method of claim 1--, therefor.

Signed and Sealed this
Twenty-first Day of June, 2016

Michelle K. Lee
*Director of the United States Patent and Trademark Office*